(12) United States Patent
Kroner

(10) Patent No.: US 7,295,004 B2
(45) Date of Patent: Nov. 13, 2007

(54) EDDY CURRENT PROBE AND METHOD OF MANUFACTURE THEREOF

(76) Inventor: Gary Kroner, 3318 Oaknoll Rd., Gibsonia, PA (US) 15044

( * ) Notice: Subject to any disclaimer, the term of this patent is extended or adjusted under 35 U.S.C. 154(b) by 65 days.

(21) Appl. No.: 11/368,042

(22) Filed: Mar. 3, 2006

(65) Prior Publication Data

US 2007/0205764 A1  Sep. 6, 2007

(51) Int. Cl.
*G01N 27/90* (2006.01)
*G01R 33/12* (2006.01)
(52) U.S. Cl. .................. 324/220; 324/240; 324/238
(58) Field of Classification Search ......... 324/219–241
See application file for complete search history.

(56) References Cited

U.S. PATENT DOCUMENTS

| | | | |
|---|---|---|---|
| 4,608,534 A | 8/1986 | Cecco et al. | |
| 4,649,343 A | 3/1987 | Birchak et al. | |
| 4,742,298 A | 5/1988 | Ando et al. | |
| 4,806,863 A | 2/1989 | White | |
| 4,808,924 A | 2/1989 | Cecco et al. | |
| 4,808,927 A | 2/1989 | Cecco et al. | |
| 4,810,966 A * | 3/1989 | Schmall ................. | 324/207.17 |
| 5,047,719 A * | 9/1991 | Johnson et al. ............. | 324/242 |
| 5,600,240 A * | 2/1997 | Mikhailovich et al. ..... | 324/219 |
| 5,717,332 A * | 2/1998 | Hedengren et al. ......... | 324/229 |
| 6,954,065 B2 * | 10/2005 | Shoji .......................... | 324/240 |
| 7,235,967 B2 * | 6/2007 | Nishimizu et al. .......... | 324/239 |
| 2005/0007106 A1 * | 1/2005 | Goldfine et al. ............ | 324/228 |

* cited by examiner

*Primary Examiner*—Jay M Patidar
(74) *Attorney, Agent, or Firm*—The Webb Law Firm

(57) ABSTRACT

An eddy current probe includes a plurality of deformable substrates each having a pair of coils wound coaxially thereabout in spaced relation and a housing supporting said plurality of substrates adjacent to each other with each substrate compressed in a direction laterally to the axis of the pair of coils wound thereabout. Desirably, the axis of each pair of coils is positioned spaced from a longitudinal axis of the housing and parallel to a tangent to an exterior surface of the housing.

18 Claims, 4 Drawing Sheets

EDDY CURRENT PROBE AND METHOD OF MANUFACTURE THEREOF

BACKGROUND OF THE INVENTION

1. Field of the Invention

The present invention relates to eddy current probes for inspection of tubes or other cylindrical components and, more particularly, to probes for providing defect signals which may be distinguished from noise signals.

2. Description of Related Art

Conventional eddy current probes have been found useful for detecting flaws and defects in tubes, pipes or other cylindrical components. Examples of prior art eddy current probes are disclosed in U.S. Pat. No. 4,608,534 to Cecco et al.; U.S. Pat. No. 4,808,927 to Cecco et al.; U.S. Pat. No. 4,742,298 to Ando et al.; U.S. Pat. No. 4,806,863 to White; U.S. Pat. No. 4,649,343 to Birchak et al.; and U.S. Pat. No. 4,808,924 to Cecco et al.

While prior eddy current probes are capable of detecting where along the length of a tube, pipe or other cylindrical component a flaw or defect may exist, heretofore, these prior art eddy current probes are not effective for pinpointing the location of the flaw or defect in the circumference of the tube, pipe or other cylindrical component.

What is, therefore, needed is an eddy current probe that overcomes the above problem and others and which enables the identification of flaws or defects in a pipe, a tube or other cylindrical component along its length and circumference. Still other problems the present invention overcomes will become apparent to those of ordinary skill in the art upon reading and understanding the following detailed description.

SUMMARY OF THE INVENTION

The invention is an eddy current probe that includes a plurality of deformable substrates each having a pair of coils wound thereabout in spaced relation and a housing supporting said plurality of substrates adjacent to each other with each substrate compressed in a direction laterally to the axis of the pair of coils wound thereabout.

At least one of each substrate and the housing can be non-magnetic and non-conductive.

The housing can be cylindrically shaped. The plurality of substrates can be supported by the cylindrically shaped housing on or adjacent a circumference thereof. The cylindrically shaped housing can include a ring shaped slot adjacent an end thereof and each substrate can be positioned in the ring shaped slot. The plurality of substrates desirably lie on and to one side of an imaginary plane that intersects the cylindrically shaped housing laterally to an axis thereof. Each coil is desirably wound around its substrate a plurality of times. Each substrate can include a pair of spaced slots in which the pair of coils is received.

The probe can further include a non-magnetic cover surrounding the housing and the plurality of compressed substrates supported thereby.

The invention is also a method of manufacturing an eddy current probe comprising: (a) providing a plurality of ring shaped flexible substrates, with each of the substrates having on or adjacent a circumference thereof a pair of wires wound there around in spaced relation; (b) providing a housing; (c) compressing each ring shaped flexible substrate transverse to an axis thereof; and (d) installing each compressed ring shaped flexible substrate on the housing such that the compressed flexible substrate remains in a compressed state on the housing.

The housing can be configured to retain each ring shaped flexible substrate in its compressed state.

The method can further include inserting the housing having the compressed flexible substrates installed thereon in an enclosure.

The housing can be formed from a first material that is non-magnetic and non-conductive. Each substrate can be formed from a second material that is non-magnetic and non-conductive. The enclosure can be formed from a third material that is non-magnetic.

Each wire can be wound a plurality of times around its substrate. Each wire can be received in a slot formed in the substrate.

Lastly, the invention is an eddy current probe that includes a cylindrical housing defining a longitudinal axis and plural pairs of spaced coaxial coils supported by the housing with the axis of each pair of coils positioned spaced from the longitudinal axis of the cylindrical housing and parallel to a tangent to the cylindrical housing.

The axis of each pair of coils can be positioned either parallel or perpendicular to the longitudinal axis of the cylindrical housing. Each pair of coils can be non-circular around its axis. Each pair of coils can be supported by the housing via a non-circular substrate. Each substrate can be formed of an elastic material that can be deformed to the non-circular shape for supporting the pair of coils on the housing.

The housing, the plural pairs of coils and their substrates can be disposed inside an enclosure.

DETAILED DESCRIPTION OF THE INVENTION

The present invention will be described with reference to the accompanying figures where like reference numbers correspond to like elements.

Figure 1:
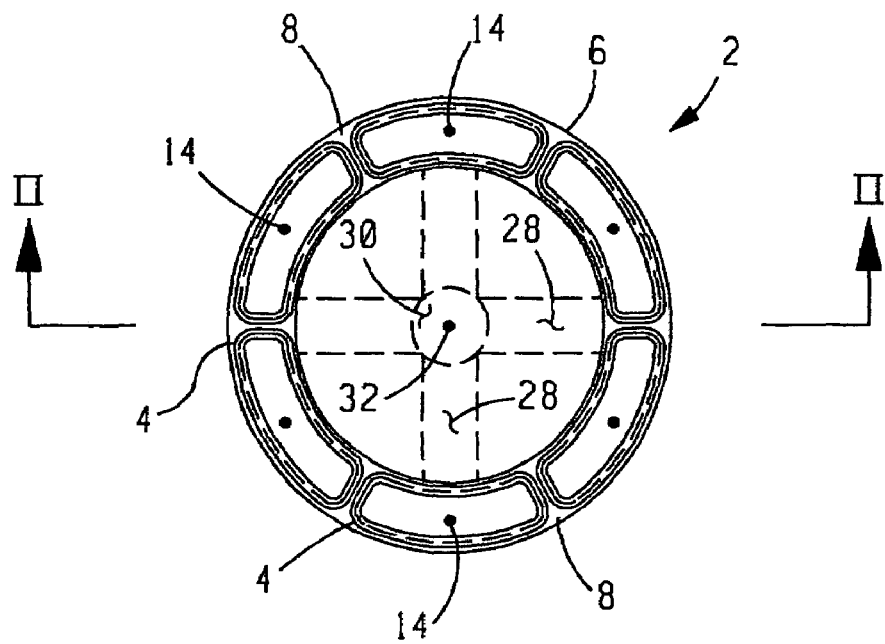
FIG. 1 is an end view of a plurality of substrates mounted or installed on or in a housing of an eddy current probe in accordance with the present invention.
Figure 2:
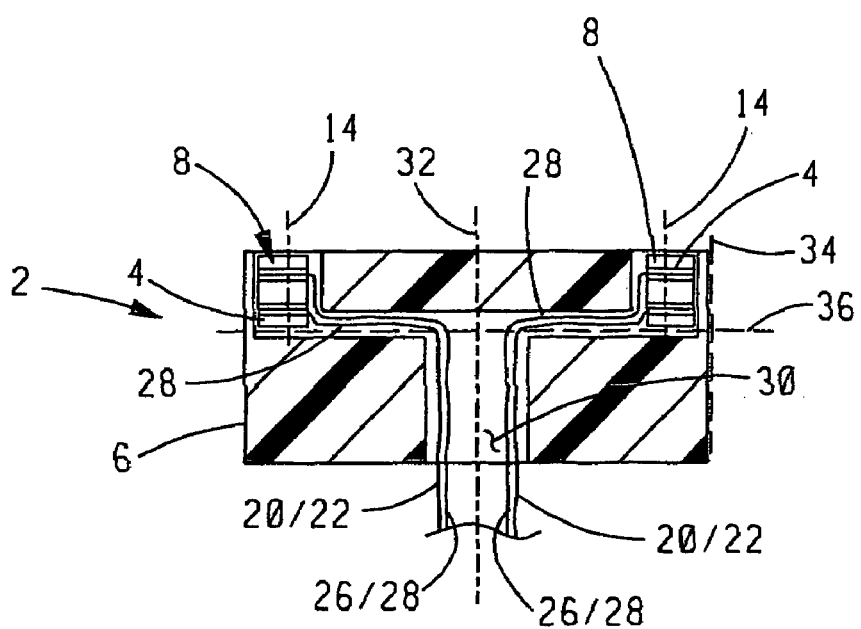
FIG. 2 is a cross section taken along lines II-II in FIG. 1.

With reference to FIGS. 1 and 2, an eddy current probe 2 in accordance with the present invention includes a plurality of deformable or flexible substrates 4 installed or mounted on a housing 6 which supports each substrate 4. Desirably, housing 6 includes a ring shaped channel or groove 8 formed therein adjacent a periphery of housing 6 adjacent one end thereof. Each substrate 4 is installed in a compressed state in channel 8 which maintains the substrate 4 in its compressed state.

Desirably, housing 6 has a cylindrical shape and the plurality of substrates 4 is positioned in channel 8 in a tightly packed circular arrangement. The description of housing 6 being cylindrical shaped and channel 8 being ring shaped, however, is not to be construed as limiting the invention since the use of any suitably shaped housing and/or channel is envisioned.

Figure 3:
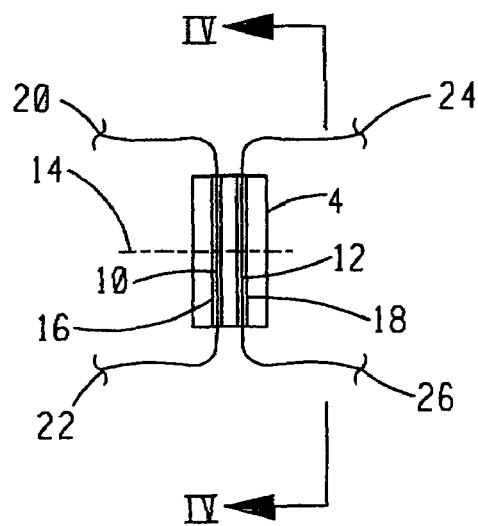
FIG. 3 is an isolated side view of a substrate of FIG. 1 prior to installation or mounting.
Figure 4:
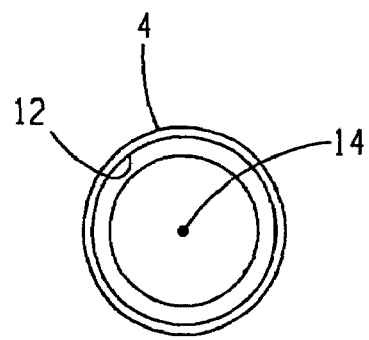
FIG. 4 is a view taken along lines IV-IV in FIG. 3.
Figure 5:
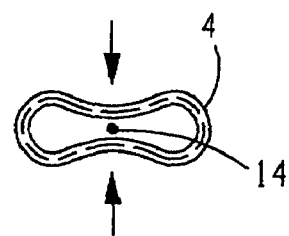
FIG. 5 is a view of the substrate shown in FIG. 4 after it has been compressed.

With reference to FIGS. 3-5 and with continuing reference to FIGS. 1 and 2, each substrate 4 includes a pair of coils 10 and 12 wound coaxially around an axis 14 of substrate 4 when substrate 4 is in its uncompressed state. Desirably, in its uncompressed state, substrate 4 is ring shaped as shown best in FIG. 4. Winding of coils 10 and 12 on substrate 4 is accomplished by first mounting substrate 4 on a bobbin (not shown) of a winding machine and thereafter winding coils 10 and 12 in spaced coaxial relation on substrate 4.

To facilitate maintaining coils 10 and 12 in spaced coaxial relation, the outer surface of substrate 4 can include a pair of spaced grooves 16 and 18 in which coils 10 and 12, respectively, are wound. Coil 10 includes a first end 20 and a second end 22 that facilitate connection of coil 10 to suitable test circuitry. Similarly, coil 12 includes a first end 24 and a second end 26 that facilitate the connection of coil 12 to suitable test circuitry.

Housing 6 includes one or more radial conduits 28 that extend between channel 8 and a bore 30 which, in the illustrated embodiment, extends from the end of housing 6 opposite channel 8 to a point intermediate the ends of housing 6.

Bore 30 and one or more conduits 28 facilitate the routing of the ends 20-26 of coils 10 and 12 of each substrate 4 inserted in channel 8 to an end of housing 6 opposite channel 8. The illustration of bore 30 and conduits 28, however, is not to be construed as limiting the invention since the ends 20-26 of coils 10 and 12 of each substrate 4 can be routed through or around housing 6 in any suitable and/or desirable manner.

In the embodiment illustrated in FIGS. 1 and 2, the axis 14 of each pair of coils 10 and 12 of each substrate 4 is positioned spaced from a longitudinal axis 32 of housing 6 and parallel to a tangent 34 to the exterior of housing 6 which, in the embodiment shown in FIGS. 1 and 2, runs parallel to longitudinal axis 32.

Figure 6:
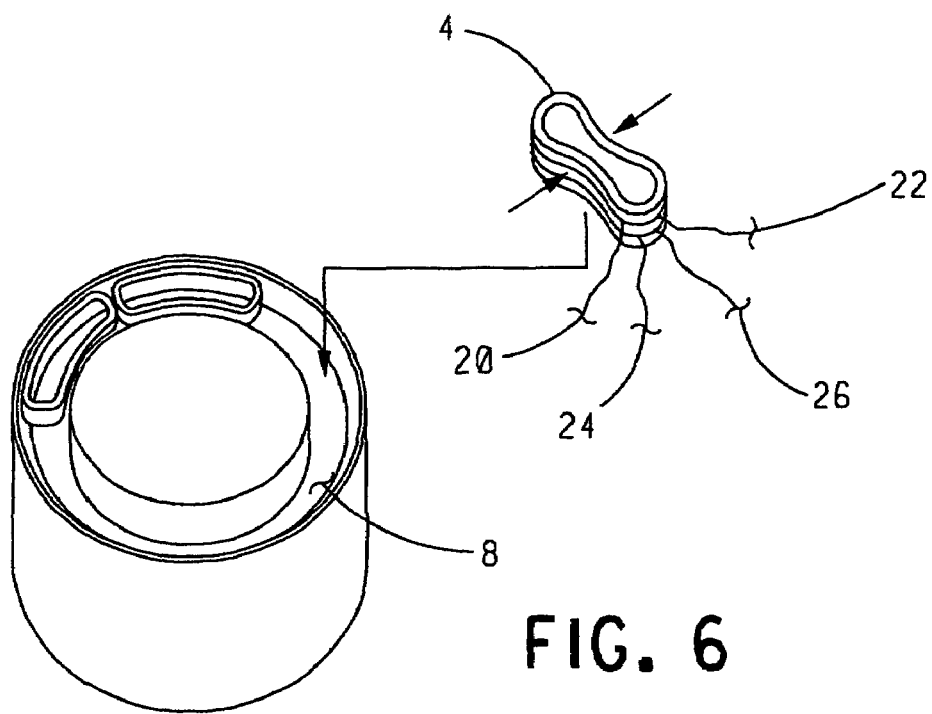
FIG. 6 is a perspective view of the housing of FIGS. 1 and 2 showing the mounting or installation of a compressed substrate thereon.

With reference to FIGS. 5 and 6 and with continuing reference to FIGS. 1-4, a method of manufacturing eddy current probe 2 will now be described. Initially, housing 6 and a plurality of ring shaped flexible substrates 4 are provided, with each substrate 4 having on or adjacent a circumference thereof a pair of wires 10 and 12 wound therearound in spaced coaxial relation. Next, each ring shaped flexible substrate 4 and its spaced coaxial coils 10 and 12 are compressed transverse, desirably laterally, to axis 14 as shown best in FIG. 5. Thereafter, each compressed flexible substrate 4 and its compressed coils 10 and 12 are installed on housing 6 such that the compressed substrate 4 and its coils 10 and 12 remain in a compressed state on housing 6. More specifically, each compressed substrate 4 and its compressed coils 10 and 12 are inserted in channel 8 of housing 6 which maintains substrate 4 and its coils 10 and 12 in an oval shaped arc, shown best in FIG. 1.

At a suitable time, ends 20-26 of coils 10 and 12 of each substrate 4 are routed through a conduit 28 and bore 30 of housing 6 to facilitate connection of said ends 20-26 to suitable testing circuitry.

Desirably, housing 6 and, more particularly, channel 8 supports each substrate 4 and its corresponding coils 10 and 12 on and to one side of an imaginary plane 36 that intersects housing 6 laterally, desirably perpendicular, to longitudinal axis 32.

In one exemplary, non-limiting embodiment, housing 6 is formed from a non-magnetic and non-conductive material, such as nylon or acetal, substrate 4 is formed from a non-magnetic, non-conductive and flexible material, such as vinyl tubing, having a length of about 0.55 inches, an outside diameter of about 0.8 inches and a wall thickness of about 0.1 inch. Each groove 16 and 18 has a width of about 0.15 inches and a depth of about 0.035 inches. Grooves 16 and 18 have their inner edges spaced from each other by about 0.06 inches. Each coil is formed of magnet wire made of approximately 99% copper. The number of turns of each coil 10 and 12 can be selected in any suitable and/or desirable manner. In one non-limiting embodiment, each coil 10 and 12 has 200 turns of wire. The foregoing dimensions are not to be construed as limiting the invention.

Figure 7:
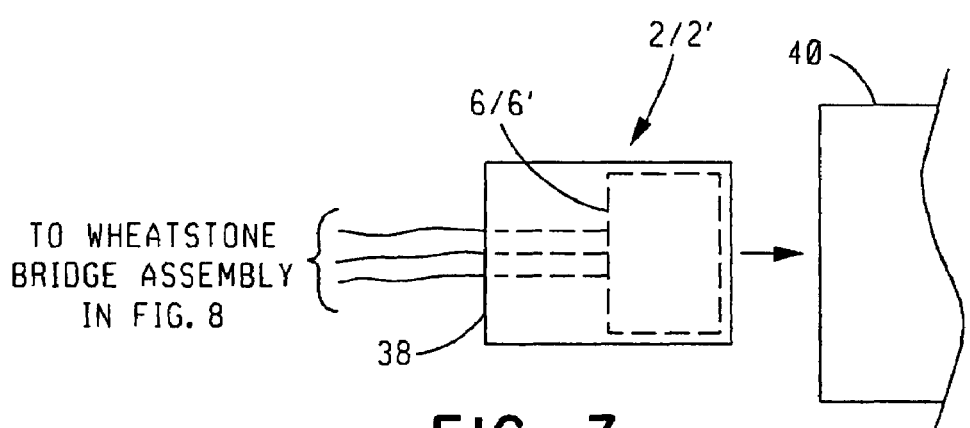
FIG. 7 is a side view showing the plurality of substrates and housing of FIGS. 1 and 2 inserted in an enclosure to form the final form of the eddy current probe of the present invention and further showing insertion of said eddy current probe into a tube to be tested thereby.

With reference to FIG. 7 and with continuing reference to FIGS. 1-6, once all of the substrates 4 have been mounted thereon, housing 6 is inserted into an enclosure 38 thereby forming the final assembly of eddy current probe 2. Enclosure 38 covers and protects housing 6 and substrates 4 installed thereon from environmental hazards. Desirably, enclosure 38 completely covers housing 6 and substrates 4 mounted thereon. However, this is not to be construed as limiting the invention.

In one exemplary, non-limiting embodiment, enclosure 38 is a sleeve formed of a non-magnetic material, such as stainless steel, having a wall thickness of about 0.015 inches. However, the use of stainless steel and the foregoing dimensions of enclosure 38 are not to be construed as limiting the invention.

In use, eddy current probe 2 is inserted into a tube 40 to be inspected by eddy current probe 2.

Figure 8:
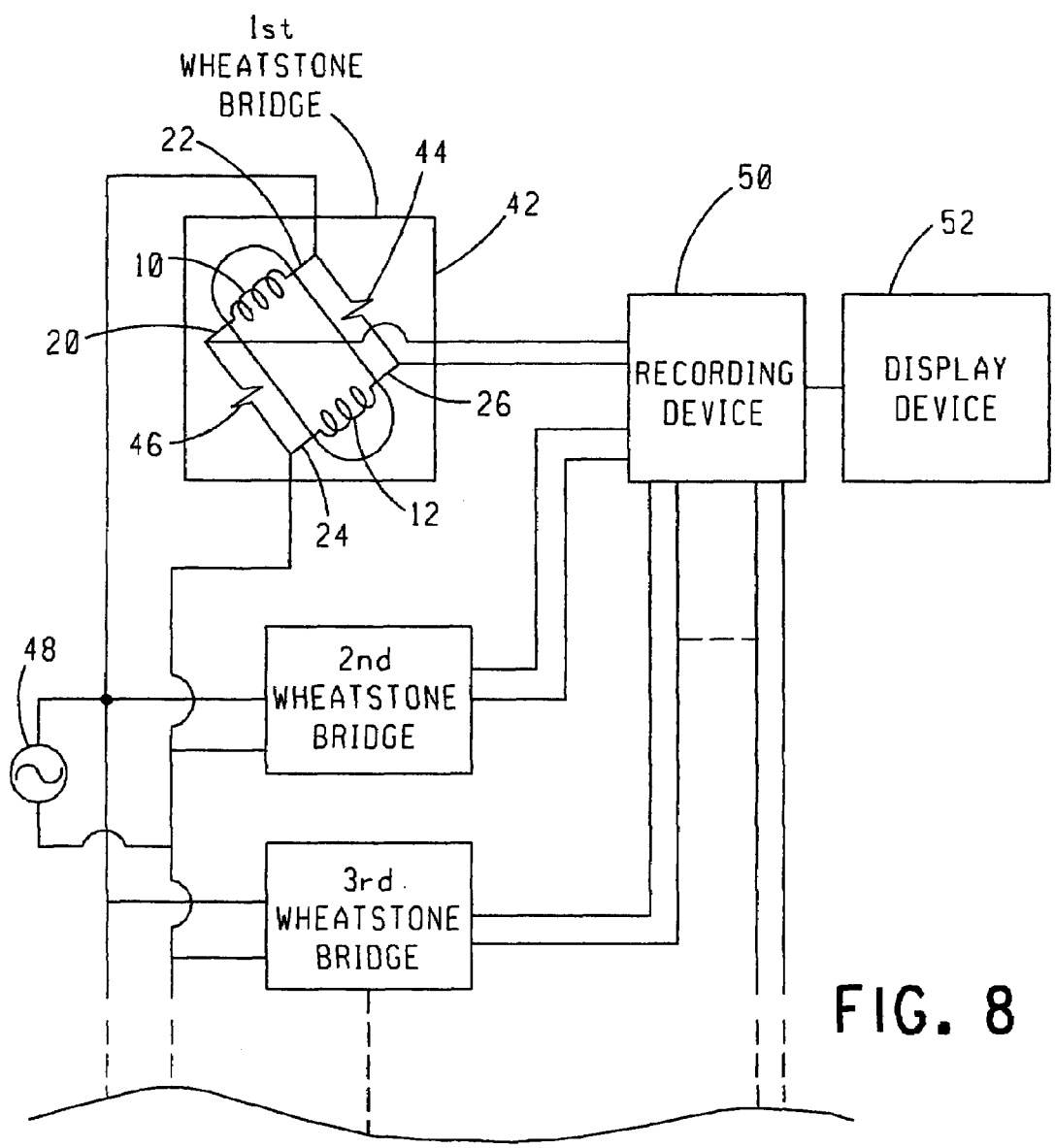
FIG. 8 is a mixed block diagram and circuit schematic view of an exemplary test system that is operative with the eddy current probe shown in FIG. 7 for detecting the presence of flaws in a tube under test.

With reference to FIG. 8 and with continuing reference to FIGS. 1-7, at a suitable time, the pair of coils 10 and 12 of each substrate 4 installed on housing 6 is coupled via ends 20-26 thereof to opposing legs of a Wheatstone Bridge 42 which has a pair of precision resistors 44 and 46 in the other legs thereof. Two opposing nodes of Wheatstone Bridge 42 are connected to an AC signal source 48 of suitable amplitude and frequency for testing tube 40. The other two nodes of Wheatstone Bridge 42 are connected to a recording device 50 which is operative for recording the time varying response of Wheatstone Bridge 42 to the AC signal output by AC signal source 48 in response to moving eddy current probe 2 through tube 40 in a manner known in the art. Specifically, each time the pair of coils 10 and 12 forming Wheatstone Bridge 42 encounter a flaw in tube 40, Wheatstone Bridge 42 outputs a corresponding signal to recording device 50. Recording device 50 can be any one of a strip chart recorder, a computer which can convert analog signals output by Wheatstone Bridge 42 into corresponding digital signal equivalents which can be processed and/or stored for subsequent retrieval and analysis, and the like. Where recording device 50 is a computer, a suitable display device 52 can be coupled to recording device 50 which can be operative for causing the output of Wheatstone Bridge 42 to be displayed on display device 52 as a function of time and/or as a function of the distance eddy current probe 2 travels in tube 40.

As shown in FIG. 8, a plurality of Wheatstone Bridges, each of which can be coupled to a different pair of coils 10 and 12 of the substrates 4 of eddy current probe 2, can be coupled to recording device 50 which can be operative for recording the output of each Wheatstone Bridge and, if desired, causing a display of said outputs versus time and/or versus position of eddy current probe 2 in tube 40 to be displayed on display device 52.

Figure 9:
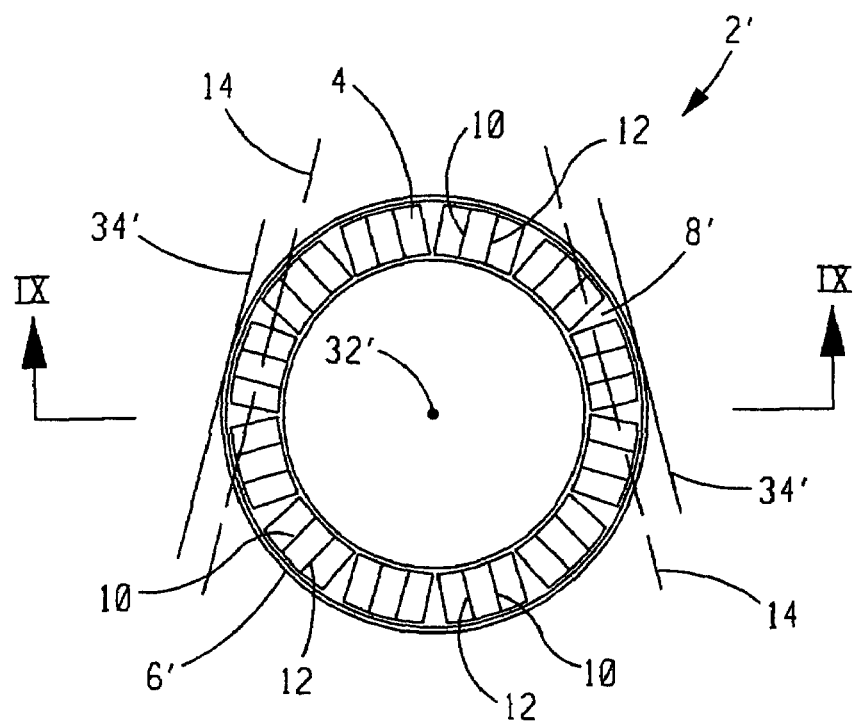
FIG. 9 is an end view of another embodiment eddy current probe in accordance with the present invention.
Figure 10:
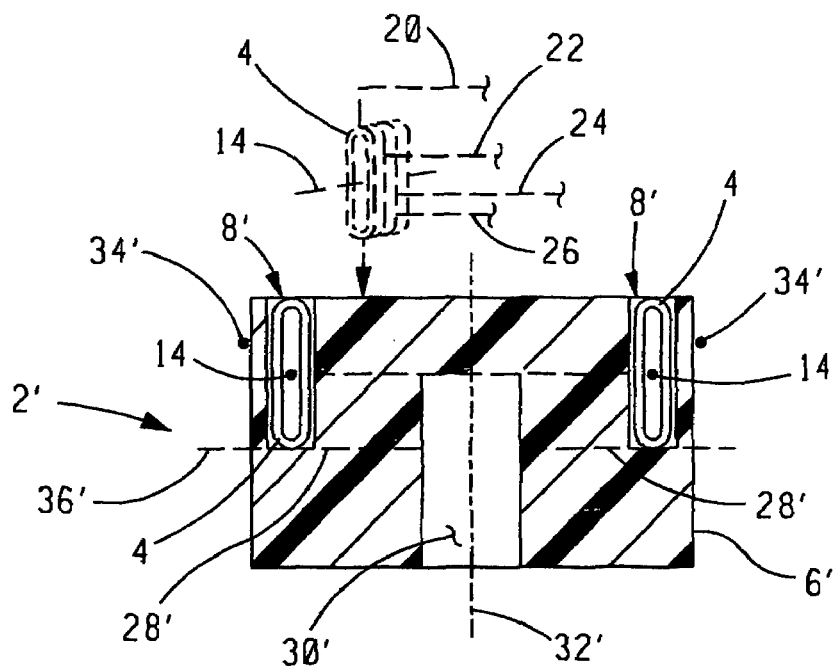
FIG. 10 is a view taken along lines IX-IX in FIG. 9.

With reference to FIGS. 9 and 10, and with continuing reference to all previous figures, another embodiment of an eddy current probe 2' includes a plurality of substrates 4, like the substrates 4 shown in FIGS. 1-6, and a housing 6'. Desirably, housing 6' has a cylindrical shape that defines a longitudinal axis 32'. Housing 6' also includes a channel or groove 8', desirably ring shaped. The primary difference between housing 6 in FIGS. 1 and 2 and housing 6' in FIGS. 9 and 10 is that channel 8' in housing 6' is deeper than channel 8 in housing 6 to accommodate a plurality of substrates 4 rotated 90° from the orientations shown in FIGS. 1 and 2 to the upright positions shown in FIGS. 9 and 10. If desired, housing 6' can also be longer than housing 6 to facilitate the formation of channel 8' therein.

When oriented in the upright position shown in FIGS. 9 and 10, the axis 14 of each substrate 4 is spaced from longitudinal axis 32' and is positioned parallel to a tangent 34' to the exterior of housing 6' that runs transverse, desirably perpendicular, to longitudinal axis 32'. Since, in FIGS. 9 and 10, the plurality of substrates 4 are positioned upright and in a tightly packed circle, the axis of each pair of coils 10 and 12 is positioned spaced from longitudinal axis 32' of housing 6' and parallel to a different tangent 34' to the exterior of housing 6'.

Housing 6', including the plurality of substrates 4 mounted or installed thereon in the manner shown in FIGS. 9 and 10, can be inserted into enclosure 38 thereby forming the final assembly of eddy current probe 2' which can be utilized in the manner discussed above in connection with eddy current probe 2. The ends 20-26 of the pair of coils 10 and 12 of each substrate 4 installed or mounted on housing 6' can be connected to a Wheatstone Bridge, like Wheatstone Bridge 42 in FIG. 8, in the manner described above for the pair of coils 10 and 12 of each substrate 4 mounted or installed on housing 6.

Like the embodiment of housing 6 and substrates 4 shown in FIG. 2, substrates 4 mounted or installed on housing 6' lie on and to one side of an imaginary plane 36' that intersects housing 6' laterally, desirably perpendicular, to longitudinal axis 32' thereof.

As shown in FIG. 10, each substrate 4 mounted or installed on housing 6' has a non-circular shape. Desirably, each substrate 4 mounted or installed on housing 6' has an oval shape.

The invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An eddy current probe comprising:
a plurality of deformable substrates each having a pair of coils wound thereabout in spaced relation; and
a housing supporting said plurality of substrates adjacent to each other with each substrate compressed in a direction laterally to the axis of the pair of coils wound thereabout.

2. The probe of claim 1, wherein at least one of each substrate and the housing is non-magnetic and non-conductive.

3. The probe of claim 1, wherein:
the housing is cylindrically shaped; and
the plurality of substrates is supported by the cylindrically shaped housing on or adjacent a circumference thereof.

4. The probe of claim 3, wherein:
the cylindrically shaped housing includes a ring shaped slot adjacent an end thereof; and
each substrate is positioned in the ring shaped slot.

5. The probe of claim 3, wherein the plurality of substrates lie on and to one side of an imaginary plane that intersects the cylindrically shaped housing laterally to an axis thereof.

6. The probe of claim 1, further including a non-magnetic cover surrounding the housing and the plurality of compressed substrates supported thereby.

7. The probe of claim 1, wherein each coil is wound around its substrate a plurality of times.

8. The probe of claim 1, wherein the pair of coils is received in a pair of spaced slots in the substrate.

9. A method of assembling an eddy current probe comprising:
(a) providing a plurality of ring shaped flexible substrates, with each of the substrates having on or adjacent a circumference thereof a pair of wires wound there around in spaced relation;
(b) providing a housing;
(c) compressing each ring shaped flexible substrate transverse to an axis thereof; and
(d) installing each compressed ring shaped flexible substrate on the housing such that the compressed flexible substrate remains in a compressed state on the housing.

10. The method of claim 9, wherein the housing is configured to retain each ring shaped flexible substrate in its compressed state.

11. The method of claim 9, further including inserting the housing having the compressed flexible substrates installed thereon in an enclosure.

12. The method of claim 11, wherein at least one of:
the housing is formed from a first material that is non-magnetic and non-conductive;
each substrate is formed from a second material that is non-magnetic and non-conductive; and
the enclosure is formed from a third material that is non-magnetic.

13. The method of claim 9, wherein each wire is wound a plurality of times around its substrate.

14. The method of claim 9, wherein each wire is received in a slot formed in the substrate.

15. An eddy current probe comprising:
a cylindrical housing defining a longitudinal axis; and
plural pairs of spaced coaxial coils supported by the housing with the axis of each pair of coils positioned spaced from the longitudinal axis of the cylindrical housing and parallel to a tangent to the cylindrical housing, wherein; each pair of coils is supported by the housing via a non-circular substrate; and each substrate is formed of an elastic material that is deformed to the non-circular shape for supporting the pair of coils on the housing.

16. The probe of claim 15, wherein the axis of each pair of coils is positioned either parallel or perpendicular to the longitudinal axis of the cylindrical housing.

17. The probe of claim 15, wherein each pair of coils is non-circular around its axis.

18. The probe of claim 15, further comprising an enclosure in which the housing, the plural pairs of coils and their substrates are received.

* * * * *